United States Patent [19]

Welton

[11] Patent Number: 5,157,205

[45] Date of Patent: Oct. 20, 1992

[54] PROCESS FOR REMOVING ALDEHYDES AND/OR VINYL ESTERS FROM GASEOUS OR LIQUID PROCESS STREAMS

[75] Inventor: Donald E. Welton, Victoria, Tex.

[73] Assignee: Occidental Chemical Corporation, Niagara Falls, N.Y.

[21] Appl. No.: 763,772

[22] Filed: Sep. 23, 1991

[51] Int. Cl.$^5$ ............................................... C07C 7/10
[52] U.S. Cl. .................................. 585/853; 585/856; 585/868; 423/245.1
[58] Field of Search ............... 585/809, 833, 856, 868, 585/853; 423/210, 210.5, 245.1, 245.2

[56] References Cited

U.S. PATENT DOCUMENTS

| | | | |
|---|---|---|---|
| 3,281,489 | 10/1966 | Goering | 585/262 |
| 3,535,399 | 10/1970 | Tabler | 585/854 |
| 4,057,575 | 11/1977 | Klass | 560/245 |
| 4,125,568 | 11/1978 | Theriot et al. | 585/856 |
| 4,161,610 | 7/1979 | Klass | 560/243 |
| 4,673,489 | 6/1987 | Roling | 585/800 |
| 4,933,499 | 6/1990 | Grotenhuis | 585/809 |
| 5,059,730 | 10/1991 | Strebelle | 570/238 |

*Primary Examiner*—Anthony McFarlane
*Attorney, Agent, or Firm*—Richard D. Fuerle

[57] ABSTRACT

Solutions of caustic and sulfite are used in a single step process to remove aldehydes and vinyl esters from gaseous and liquid process streams.

20 Claims, No Drawings

PROCESS FOR REMOVING ALDEHYDES AND/OR VINYL ESTERS FROM GASEOUS OR LIQUID PROCESS STREAMS

BACKGROUND OF THE INVENTION

It is often convenient to remove aldehydes or vinyl esters from process streams. This is desirable because aldehydes or vinyl esters such as vinyl acetate are reactive materials and may interfere with subsequent utilization of the stream. For example, in the preparation of vinyl acetate/ethylene copolymers, a stream of waste gases is produced which contains ethylene vinyl acetate, carbon dioxide and other impurities. The gas is not suitable for recycling for further production of copolymer. However, instead of burning the gas as a waste gas, it is desirable to remove the vinyl acetate as well as carbon dioxide from the gas stream and recover the ethylene which may then be used for the production of polyethylene.

One possible method for removal of vinyl esters from a gas stream is to intimately contact the gas with an aqueous basic solution. In the presence of a base, vinyl esters readily hydrolyze to form acetaldehyde and a carboxylate ion. Unfortunately, the acetaldehyde, in the presence of a base, undergoes an aldol condensation in which one molecule of acetaldehyde adds to another molecule to form a 4-carbon hydroxyaldehyde. This hydroxyaldehyde dehydrates to 2-butenal. The butenal can itself undergo condensation reactions and eventually insoluble polymeric materials are formed. These polymers can form in such quantities that the equipment must be periodically shut down for cleaning.

U.S. Pat. No. 3,465,032 discloses a process for removing formaldehyde, acetaldehyde, and butyraldehyde from vinyl acetate. This process involves treating the acetate with sodium bisulfite in order to form the addition products with the aldehyde impurities. The process is conducted at a pH range from about 4.2 to about 6.5. It is also disclosed that when a large excess of bisulfite is present, it reacts with vinyl acetate to form acetic acid and the sodium bisulfite addition product of acetaldehyde.

German Patent application DE 78-2843464 (as abstracted in CA 93:72576k) discloses that aldehydes may be removed from vinyl acetate by treatment with aqueous sodium bisulfite.

French Patent 2,647,782 (as abstracted in Derwent Acc. No. 90-363269/49, and CA 114:82726a) discloses the purification of vinyl chloride containing vinyl acetate by first washing with alkali and then treating the remaining gas with sodium bisulfite at a pH of 6.5 to 8.5. In one example, a stream of vinyl chloride containing 2500 ppm of vinyl acetate was washed with aqueous NaOH. The resultant gas stream contained less than one ppm vinyl acetate and 250 ppm acetaldehyde. This gas stream was then treated with aqueous sodium bisulfite giving a stream of vinyl chloride containing less than 1 ppm vinyl acetate and less than 1 ppm acetaldehyde and 60 ppm $SO_2$. As set forth more fully below, experiments that we have conducted show that the treatment of vinyl acetate with a caustic leads to the formation of solid polymers. In continuous applications, a buildup of such polymers would be expected in the process of French Patent 2,647,782.

The addition of sodium bisulfite to a carbonyl group is a well-known reaction (see for example, Fundamentals of Organic Chemistry, second edition, T. W. Graham Solomons, pp 621-2, John Wiley & Sons, New York, 1986). The bisulfite addition reaction occurs with aldehydes and with some ketones. The reaction to form the bisulfite addition product is reversible, and often yields a crystalline adduct. Thus, it is useful for separating aldehydes from other materials since the aldehyde can be separated as an adduct and then regenerated by adding either an acid or a base to the adduct. If an acid is used, the aldehyde is released along with $SO_2$. In basic solutions, the aldehyde is again liberated along with the production of sulfite ion. Accordingly, sodium bisulfite addition to aldehydes would not be expected to occur in strong basic solutions since the presence of a strong base would tend to decompose any adduct that formed. In addition, a strongly basic solution would drive the equilibrium away from adduct formation by converting bisulfite ions into their conjugate base, i.e., sulfite ions.

In spite of the reversibility of bisulfite addition in basic solution, it is an object of the present invention to provide a process in which a liquid or gaseous process stream containing vinyl esters such as vinyl acetate or aldehyde impurities is treated with sodium sulfite and base in a single step. It is desirable to conduct the treatment in a strongly basic solution so that any vinyl esters, such as vinyl acetate, will be hydrolyzed and removed along with the aldehyde impurities. If the treatment solution is not strongly basic, the vinyl esters are not hydrolyzed rapidly enough to allow their efficient removal, along with aldehyde impurities, in a single step. Such a process is simpler than the two step process of French Patent 2,647,782, and since it is conducted in a highly basic solution, does not leave impurities of $SO_2$ in the product gas. Furthermore, it is more economical since it requires no more than 0.5 mole of sulfite for each mole of vinyl acetate or aldehyde removed, compared to the 1 or more moles of bisulfite required by prior art processes.

SUMMARY OF THE INVENTION

Surprisingly, it has now been found that sulfite ion reacts with aldehydes in strongly basic solutions. Accordingly, a source of sulfite ion such as sodium sulfite can be used in a caustic (basic) solution for the removal of vinyl esters such as vinyl acetate and aldehydes from liquid or gaseous process streams. Foaming is suppressed by proper control of the pH and the amount of sulfite present, and insoluble polymers are not formed.

DETAILED DESCRIPTION OF THE INVENTION

Surprisingly, it has now been found that sodium sulfite ion reacts with aldehydes in strongly basic solutions. As opposed to the formation of the sodium bisulfite adduct, which is reversible in both acid and basic solutions, the reaction product formed in basic solution between sodium sulfite and aldehyde is formed irreversibly. Accordingly, a source of sulfite ion such as sodium sulfite may be used in a caustic (basic) solution for the removal of vinyl esters such as vinyl acetate and aldehydes from liquid or gaseous process streams. Suitable bases are metal hydroxides. Because of considerations of cost and availability, the preferred base is sodium hydroxide. Any soluble source of sulfite ion is suitable for use in the present invention. The preferred source of sulfite is sodium sulfite.

We have found that when vinyl acetate or acetaldehyde is added to a strongly basic solution containing sodium sulfite, the reversible bisulfite-type adducts described in prior art are not formed. Instead, products of permanent stability were rapidly formed, and solids deposition was totally prevented. In subsequent tests to determine the amount of sodium sulfite needed to prevent solids deposition, varying amounts of sodium sulfite were added to aqueous caustic solutions to which liquid vinyl acetate or acetaldehyde was then added. Surprisingly, while the sulfite-free controls became cloudy with red solids within a half hour, every test using mole ratios of sodium sulfite to vinyl acetate of 0.2 or higher remained clear for a full year's observation. Similar phenomena were observed when solutions of vinyl acetate in an immiscible liquid such as hexane were used in place of pure vinyl acetate or acetaldehyde. In this case, the mole ratio is the ratio of the number of moles of sulfite to the number of moles of vinyl acetate added.

During subsequent experimental tests in a large scale scrubber, with recirculating caustic-sulfite liquor removing vinyl acetate from ethylene, it was found that severe foaming of the scrubber was encountered at low mole ratios of sulfite to vinyl acetate, but could be prevented by maintaining the mole ratio of sulfite to aldehyde at 0.5 (±0.1). See Examples 4 and 5. In a large scale scrubber, the mole ratio of aldehyde or vinyl acetate to sulfite is a bit more difficult to describe. The gas stream proceeds through the scrubber, and is exposed to the aqueous caustic sulfite solution. From the pressure and flow rate of the gas, and the flow rate of the caustic sulfite solution through the scrubber, it is possible to calculate the amount of gas, and the amount of caustic sulfite solution which move through the scrubber in a given unit of time. The mole ratio of aldehyde or vinyl acetate to sulfite may then be calculated by comparing the number of moles of vinyl acetate and aldehyde in the volume of the gas process stream which goes through the scrubber in a given unit of time, compared to the amount of sulfite in the caustic sulfite solution which moves through the scrubber in the same unit of time.

In the present process, the aqueous caustic sulfite solution is brought into intimate contact with the process stream to be purified. Aldehydes present in the process stream are extracted into the aqueous solution. Vinyl esters are hydrolyzed to form acetaldehyde which is also extracted into the aqueous solution. As noted above, aldehydes undergo aldol condensation in basic solutions.

In order to achieve the purpose of this invention, which is to remove either vinyl esters, such as vinyl acetate, and aldehydes or both vinyl esters and aldehydes, from gas or liquid process streams in a single step, the aqueous scrubbing solution must be sufficiently basic to cause rapid hydrolysis of vinyl esters and aldolization of aldehydes. We have found that the pH of the solution emerging from the scrubber or extractor (in the case of a liquid process stream) should be 12 or above. We have found that a solution of about pH of 14 contains about the highest practical concentration for the base. In these basic solutions, the vinyl esters will hydrolyze quickly. However, the aldehydes formed during hydrolysis and the aldehydes in the process stream react more slowly. They are carried along in the scrubbing solution and continue to react after the scrubbing process is completed.

The process streams that are suitable for the treatment of this invention are those that will not be harmed by the presence of water or caustic, or by the reducing action of sulfite ion. Both gas and liquid process streams can be treated by the process of the present invention. If the process stream being treated is a liquid, obviously, the liquid being treated should be practically immiscible with water. Since the properties of water, caustics, and sodium sulfite ion are well-known, those skilled in the art will have little difficulty in determining whether the process of the present invention is suitable for use with their particular process stream.

The invention can be practiced as a batch process in that a given volume of the process stream to be purified is intimately contacted with a corresponding volume of caustic sulfite solution. This is more feasible with liquid process streams than with gaseous process streams. However, the continuous processes described below are preferred to the batch process.

The invention can be practiced in any caustic scrubber suitable for scrubbing a gaseous process stream with an aqueous solution of a basic material. Such scrubbers are well-known to those skilled in the art. As an example, when the invention is being used for scrubbing a gas stream such as ethylene-containing vinyl acetate, a tubular scrubber containing polypropylene saddles has been found to be adequate. The gas stream is introduced at the bottom, and the sodium sulfite caustic solution is introduced at the top of the scrubber. However, the invention is not limited to a particular type of scrubber but will work with any type that provides for adequate contact between the scrubbing solution and the gas.

The invention can also be practiced with a liquid process stream. In this case, the caustic sulfite solution (the extractant solution) and the liquid process stream should be brought into contact with each other in an extractor suitable for use with basic solutions. Since the extractant solution and the process stream are relatively immiscible with one another, their separation after extraction can be accomplished using a settling tank or other device for separating liquid phases. The type of device used to force mixing between the liquid process stream and the liquid caustic solution, as well as the separating device, should be suitable for liquid-liquid extraction. Such extractors are well-known to those skilled in the art. As in the case of gases, the invention is not limited to a particular type of extractor.

We have found that the most practical way to conduct the process of this invention is to run the process as a continuous, steady-state process with recirculating caustic sulfite solution. This can be accomplished by having the caustic sulfite solution in a large holding tank, and conducting it to the scrubber or extractor where it countercurrently contacts the stream to be purified. We prefer to use a holding tank with a nominal holding time of at least 30 minutes. Periodically or continuously, a portion of the caustic sulfite solution is removed from the holding tank and makeup base and sulfite solutions are added at a rate calculated to maintain constant volume and the desired excess of unreacted caustic and sulfite.

The concentration of sodium sulfite and base in the caustic sulfite solution fed to the scrubber or extractor should be carefully controlled. Clearly, the presence of both unreacted caustic and unreacted sulfite must be maintained in the solution leaving the scrubber. Free caustic to maintain pH greater than 12 is essential to both hydrolyzing vinyl acetate and aldolizing acetaldehyde to unsaturated aldehydes at economically favorable rates. The feedrate of caustic fed to the scrubber must be at least 1:1 mole ratio to vinyl acetate. Unreacted sulfite must also be present in the scrubber feed to provide a feed mole ratio to vinyl acetate of at least 0.2:1, preferably at least 0.5:1.

After the scrubbing solution has gone through the scrubber, and come in contact with the process stream to be purified, some of the base can have been consumed in hydrolysis of the vinyl esters and some sulfite can have been consumed in reacting with aldehydes. The volume of the holding tank should be large enough so that the return of the scrubbing solution to the tank will not cause large fluctuations in the concentration within the tank. By considering the composition and volume of the stream to be treated, those skilled in the art will be able to calculate a proper tank size and how frequently the addition of the make up solution is to be added.

As illustrated in Example 4, if too little sodium sulfite is used, the formation of solid polymer is still suppressed, but foaming is likely to occur, and this foaming makes further processing extremely difficult. On the other hand, large quantities of sodium sulfite are costly, and, in order to keep the process as economical as possible, it is desirable to use as the minimum concentration of sodium sulfite allowing operation without either solids deposition or operational problems from foaming in the scrubber. In one application we have found that maintaining at least 1,000 ppm free sodium sulfite in the solution satisfied these requirements, although the required levels would be expected to change with process stream composition and flow, as well as with operating parameters for the scrubber, such as temperature, pressure, tank volumes and volumetric feedrate of solution. Occasionally, when sodium sulfite is present at the proper levels, some foaming will result. The cause of this condition is unknown, and it does not occur frequently. Furthermore, when proper amounts of sulfite are present, the foam can be readily controlled by the addition of a silicon-based anti-foaming agent.

EXAMPLES

EXAMPLE 1

Several comparative laboratory tests were made at 25° C. to compare changes in appearance, especially the appearance of haziness or cloudiness in test samples with time for aqueous NaOH-vinyl acetate solutions with and without added sodium sulfite. The test solutions were made from aqueous solutions of 1.0 molar sodium hydroxide, 1.0 molar sodium sulfite, and ACS grade liquid vinyl acetate (VA). Based on mole ratios of each component to VA ("R") desired, bottles were charged with calculated amounts of caustic and either sodium sulfite solution or a corresponding volume of water. Liquid vinyl acetate was then charged from a syringe, the bottles were sealed and shaken until the solution became clear (less than a minute in all cases), then observed while standing at 25° C.

Experiment 1-Initial VA concentration in solution=0.36 molar
  Control: No sulfite, R for NaOH=1.33
  Test: Both sulfite and NaOH, R=1.33 for each The VA concentration in these tests was 0.36 molar. The control solution became deep yellow in less than 10 minutes and turbid in less than 60 minutes, whereas the test solution remained clear and colorless. In 24 hours, the control solution was deep yellow with dark red suspended and settled solids; the test solution was deep yellow but totally clear and free of any trace of solids. After 4 days both solutions had deepened in color; the solids in the control solution had largely settled, but the test solution remained free of solids. Both solutions subsequently remained visually unchanged for over a year.

Experiment 2-Initial VA concentration in solutions=0.57
  Control: No sulfite, R for NaOH=1.03
  Test R for sulfite=0.67, R for NaOH=1.03

In spite of only a slight excess NaOH over that needed to combine with acetate ion from hydrolysis of VA, in this test the pH was high enough to produce aldolization of the acetaldehyde and, in the control sample without sulfite, to form a precipitated haze at less than 40 minutes and a gummy red floc in less than 24 hours. The test sample containing sulfite became yellowish in about 60 minutes and orange-red by 4 days, but remained perfectly clear.

Similar results were obtained when R for caustic/VA was increased to 1.5 and R for sulfite/VA was increased to 2.0, except that the test solution containing sulfite was much paler throughout; pale orange after more than a week.

Experiment 3-Initial VA concentration in solution=0.54
  Control: No sulfite, R for NaOH=1.25
  Test #1: R for sulfite=0.10, R. for NaOH=1.25
  Test #2: R for sulfite=0.20, R for NaOH=1.25
  Test #3: R for sulfite=0.40, R for NaOH=1.25

The control became cloudy by 5 minutes. #1 was hazy by 30 minutes, showing that 0.1 R for sodium sulfite was insufficient to prevent deposition of solids. #2 and #3 became orange-red but remained clear for at least 12 days.

This experiment, together with experiments #2 and #2, above, show that the minimum mole ratio, R, of $Na_2SO_3$/VA needed to prevent even long-term precipitation of solids from caustic VA reactions is between 0.1 and 0.2.

EXAMPLE 2

A series of laboratory tests were made to determine the expected consumption of sulfite per mole of VA or acetaldehyde hydrolyzed, particularly as related to concentration and mole ratios to VA. In these tests, 10-20 millimoles of VA were added to solutions containing both caustic and sodium sulfite. The caustic/VA mole ratio ranged from 1.0 to 2.0, while the sulfite/VA mole ratio was varied from 0.1 to 1.25. The total volume was varied from 38 ml to 100 ml. Caustic ratio was found to be of no importance as long as it was initially at least 1.0; also, there was no significant change with concentration. As expected, the dominant variable was found to be the initial sulfite/VA mole ratio, R. At R=0.1 and 0.2, over 99% of the sulfite was consumed. At R=0.5, approximately 85% was consumed, requiring only about 30 minutes to stabilize, resulting in a consumption of 0.43 ±0.2 moles of sulfite/mole of VA. At R=1.0, consumption was 0.47-0.50 mole of sulfite/mole VA, for a utilization of only 47%-50%. Corresponding results were obtained when acetaldehyde was substituted for VA.

These tests demonstrated that there is no economic incentive to feed more than about 0.5 mole of sulfite per mole of VA or aldehyde in the process stream to be purified.

EXAMPLE 3

A series of laboratory tests were made to demonstrate the applicability of caustic-sulfite solutions to extractions of liquid process streams. A solution of VA in hexane was used as an example of a typical liquid solvent stream from which one might wish to extract aldehydes or vinyl acetate. The chemistry was found to be the same as if VA or acetaldehyde had been absorbed from a gas phase. Since the distribution coefficient for acetaldehyde between water and hexane is highly in favor of water (approximately 6.7 water/hexane), transfer to the water phase was rapid, chemistry was the same, and reaction rates were very comparable to those of the previous examples. VA, however, has a distribution highly in favor of hexane (approximately 8.3 hexane/water), so that slower reaction would be expected. Surprisingly, when a solution of 1.0 volume % VA in hexane reacted with an equal volume of a water solution containing NaOH and sodium sulfite at mole ratios to VA of 2.0/0.5/1.0, the VA was 95% removed from the hexane in 5 minutes, and in 30 minutes was completely gone, while residual acetaldehyde had been reduced to less than 100 ppm. No emulsions were encountered in 20 hours of mixing.

When sulfite was omitted in an otherwise identical experiment, reaction rates of both VA and aldehyde were not significantly affected, but substantial amounts of hexane-soluble aldol oligomers appeared in the hexane, and some persistent interface emulsions were formed in less than 2 hours. These experiments demonstrate the advantages of caustic-sulfite over caustic alone as extractant.

EXAMPLE 4

Process scale testing of the effectiveness of the invention in a continuous process was done in a larger caustic scrubber. The process stream which was treated contained approximately 0.8 wt % vinyl acetate mixed with ethylene, carbon dioxide and other gases.

The installation consisted of (1) facilities for feeding caustic solution and water and for purging spent solution, all at controlled continuous flowrates, (2) a holdup tank sized to permit a nominal residence time of at least 30 minutes for the recirculating solution (3) a pump to feed the solution from the tank to the scrubber, and (4) a packed scrubbing tower equipped with a gas inlet at the bottom and exit at the top, with a separate liquid feedline at the top and drain for return of the liquid to the tank at the bottom. The system was operated at nominal 50 psig and 35°-40° C.

Facilities were installed to continuously inject sodium sulfite solution into the scrubber feedline. In order to minimize sulfite cost, the nominal sulfite to vinyl acetate mole ratio was set at 0.3. Sodium hydroxide was added to maintain a pH of 12-13. Foaming problems in the scrubbing section were immediately encountered. Addition of a widely-used silicone-type defoamer successfully alleviated the problem and the desired elimination of VA-derived solid polymers was achieved. However, over several months the defoamer deposited solids of its own, necessitating a cleaning. While the solids were soft and easily removed, the desired total freedom from solids deposition was not achieved. The gas stream emerging from the scrubber contained less than 1 ppm of acetaldehyde or vinyl acetate.

EXAMPLE 5

Surprisingly, when the feedrate of sodium sulfite to the polyethylene plant caustic scrubber described in Example 4 was increased to 0.5 mole ratio to VA, foaming was completely eliminated and no defoamer was required. The scrubber was subsequently operated continuously for over nine months with no further problems. It was shut down and opened for examination, which disclosed the complete absence of any solids anywhere in the system.

COMPARATIVE EXAMPLE 1

The scrubber of Example 4 was used to process the same process stream as used in Example 4. The process was identical of that of Example 4 except that the scrubber solution did not contain sodium sulfite. Although the scrubber successfully reduced the residual vinyl acetate and acetaldehyde levels to less than 1 ppm, the scrubber and the storage tank were heavily fouled with red solid.

I claim:

1. A process for the removal of aldehydes or vinyl esters from a gaseous process stream or a water-immiscible liquid process stream comprising
   A) contacting said gaseous or liquid process stream with an aqueous caustic sulfite solution containing at least 0.2 moles of sulfite ion per mole of said aldehydes or containing 0.2 moles of sulfite ion per mole of said vinyl esters; and
   B) separating said aqueous caustic sulfite solution from said process stream, provided that the aqueous caustic sulfite solution contains sufficient base so that the pH if the aqueous caustic sulfite solution, after it is separated from the process stream, is 12 or above.

2. A process according to claim 1 wherein said process is conducted as a batch process.

3. A process according to claim 1 wherein said process is conducted as a continuous process.

4. A process according to claim 3 in which the base is sodium hydroxide and the source of sulfite ion is sodium sulfite.

5. A process according to claim 4 wherein the process stream is gaseous.

6. A process according to claim 5 wherein the process stream comprises a mixture of ethylene and vinyl acetate.

7. A process according to claim 5 wherein the process stream comprises a mixture of ethylene and aldehydes.

8. A process according to claim 3 wherein the process stream is liquid.

9. A process according to claim 8 wherein the process stream comprises a mixture of ethylene and vinyl acetate.

10. A process according to claim 8 wherein the process stream comprises a mixture of ethylene and aldehydes.

11. A method of removing aldehydes and/or vinyl esters from a gaseous or liquid process stream comprising
    A) contacting said stream with an aqueous caustic solution containing sufficient caustic to maintain pH of at least 12 and having a sulfite ion concentration of at least 0.2 moles per mole of said aldehydes and having a sulfite ion concentration of at least 0.2 moles per mole of said vinyl esters, whereby said caustic hydrolyzes said vinyl esters to form additional aldehydes, aldehydes aldolize to form unsaturated aldehydes, and unsaturated aldehydes irreversibly react with said sulfite ion to form products soluble in said aqueous caustic solution; and B) separating said aqueous caustic solution from said process stream.

12. A method according to claim 11 wherein said process stream is waste gases from the preparation of vinyl acetate/ethylene copolymers.

13. A method according to claim 11 wherein vinyl acetate is present in said process stream.

14. A method according to claim 11 wherein the mole ratio of said caustic solution to said vinyl acetate is at least 1:1.

15. A method according to claim 13 wherein the mole ratio of said sulfite ion to said vinyl acetate is at least 0.5:1.

16. A method according to claim 11 wherein the source of said sulfite ion is sodium sulfite.

17. A method according to claim 11 wherein after said aqueous caustic solution has contacted said process stream, said aqueous caustic solution contains unreacted caustic and unreacted sulfite.

18. A method of removing vinyl acetate from a gas comprising
  A) preparing an aqueous solution that comprises
    1) water;
    2) sufficient sodium hydroxide to maintain the pH of said solution at least 12; and
    3) at least 0.2 moles of sodium sulfite per mole of vinyl acetate present in said gas;
  B) contacting said gas with said aqueous solution, whereby said vinyl acetate hydrolyzes to acetaldehyde, said acetaldehyde aldolizes to form unsaturated aldehydes, and said sulfite reacts with said unsaturated aldehydes to form products that dissolve in said aqueous solution.

19. A method according to claim 18 wherein said gas is a vinyl acetate waste stream.

20. A method according to claim 18 wherein the mole ratio of said sulfite to said vinyl acetate is maintained at 0.5±0.1.

* * * * *